United States Patent
Tsuchikawa et al.

(10) Patent No.: US 8,461,332 B2
(45) Date of Patent: Jun. 11, 2013

(54) METHOD FOR PRODUCING CURING AGENT HAVING ACIDIC SUBSTITUENT AND UNSATURATED MALEIMIDE GROUP, THERMOSETTING RESIN COMPOSITION, PREPREG, AND LAMINATE

(75) Inventors: Shinji Tsuchikawa, Ibaraki (JP); Masanori Akiyama, Ibaraki (JP); Hikari Murai, Ibaraki (JP)

(73) Assignee: Hitachi Chemical Company, Ltd., Tokyo (JP)

( * ) Notice: Subject to any disclaimer, the term of this patent is extended or adjusted under 35 U.S.C. 154(b) by 0 days.

(21) Appl. No.: 13/527,995

(22) Filed: Jun. 20, 2012

(65) Prior Publication Data
US 2012/0316263 A1   Dec. 13, 2012

Related U.S. Application Data

(62) Division of application No. 12/303,627, filed as application No. PCT/JP2007/061193 on Jun. 1, 2007.

(30) Foreign Application Priority Data

Jun. 6, 2006  (JP) ................. 2006-157168
Oct. 3, 2006  (JP) ................. 2006-271950

(51) Int. Cl.
*C07D 251/48* (2006.01)
*C07D 207/452* (2006.01)

(52) U.S. Cl.
USPC ................... 544/205; 548/520

(58) Field of Classification Search
None
See application file for complete search history.

(56) References Cited

U.S. PATENT DOCUMENTS

| 4,128,598 A | 12/1978 | Makino et al. |
| 4,196,109 A | 4/1980 | Laganis et al. |
| 5,122,590 A | 6/1992 | Camberlin et al. |

FOREIGN PATENT DOCUMENTS

| EP | 0 011 049 | 9/1979 |
| JP | 52-051499 | 4/1977 |
| JP | 53-124597 | 10/1978 |
| JP | 56-055421 | 5/1981 |
| JP | 56-059834 | 5/1981 |
| JP | 57-002328 | 1/1982 |
| JP | 57-028129 | 2/1982 |
| JP | 57-038851 | 3/1982 |
| JP | 57-080424 | 5/1982 |
| JP | 59-041358 | 3/1984 |
| JP | 59041358 A | * 3/1984 |
| JP | 59-187056 | 10/1984 |
| JP | 60-031521 | 2/1985 |
| JP | 60-210685 | 10/1985 |
| JP | 61-072023 | 4/1986 |
| JP | 62-132915 | 6/1987 |
| JP | 62-177033 | 8/1987 |
| JP | 62-46584 | 10/1987 |
| JP | 62-61051 | 12/1987 |
| JP | 63-34899 | 7/1988 |
| JP | 01-123831 | 5/1989 |
| JP | 02-024324 | 1/1990 |
| JP | 02-258820 | 10/1990 |
| JP | 02-294361 | 12/1990 |
| JP | 03-145476 | 6/1991 |
| JP | 6-8342 | 2/1994 |
| JP | 06-032969 | 2/1994 |
| JP | 08-295723 | 11/1996 |
| JP | 10-067942 | 3/1998 |
| JP | 2001-011672 | 1/2001 |

OTHER PUBLICATIONS

English translation of JP59041358, published Mar. 7, 1984.*
Japanese Official Action dated Oct. 9, 2012, for JP Application No. 2007-144877.
Matsuda et al, Abstract Translation on East, JP 59-187056, Oct. 24, 1984.
English Translation of JP 59041358, published Mar. 7, 1984.

* cited by examiner

*Primary Examiner* — Michael Barker
(74) *Attorney, Agent, or Firm* — Antonelli, Terry, Stout & Kraus, LLP.

(57) ABSTRACT

A method for producing a curing agent having an acidic substituent and an unsaturated maleimido group, including reacting, in an organic solvent, a maleimide compound (a) having at least two N-substituted maleimido groups in a molecule thereof with an amine compound (b) having an acidic substituent (represented by formula (I) below); a thermosetting resin composition containing the curing agent (A) produced through the method and a compound (B) which is cured with the curing agent, wherein a cured product of the composition has a glass transition temperature of 200° C. or higher; and a prepreg and a laminated sheet produced therefrom. The thermosetting resin composition can produce a prepreg or laminated sheet exhibiting excellent performance suitable for a printed wiring board for electronic devices and similar devices.

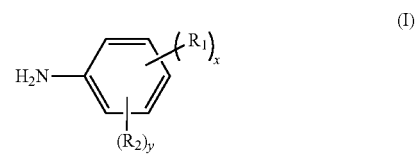

(I)

6 Claims, No Drawings

METHOD FOR PRODUCING CURING AGENT HAVING ACIDIC SUBSTITUENT AND UNSATURATED MALEIMIDE GROUP, THERMOSETTING RESIN COMPOSITION, PREPREG, AND LAMINATE

This application is a Divisional application of prior application Ser. No. 12/303,627, having a filing date of Dec. 5, 2008, the contents of which are incorporated herein by reference in their entirety. Ser. No. 12/303,627 is a National Stage Application filed under 35 USC 371, of International (PCT) Application No. PCT/JP2007/061193, filed Jun. 1, 2007.

TECHNICAL FIELD

The present invention relates to a method for producing a curing agent having an acidic substituent and an unsaturated maleimido group (hereinafter may be referred to simply as a "curing agent of the present invention"); to a thermosetting resin composition; to a prepreg; and to a laminated sheet. More particularly, the present invention relates to a method for producing a curing agent having improved solubility in an organic solvent; to a thermosetting resin composition which contains a curing agent produced through the method, which is well-balanced in all of adhesion-to-copper foil property, heat resistance, moisture resistance, flame retardancy, heat resistance of a copper-clad product whose substrate is formed from the composition (hereinafter may be referred to as "copper cladding heat resistance"), and dielectric properties (relative dielectric constant and dielectric loss tangent), and which is useful for forming a printed wiring board for electronic devices; to a prepreg formed from the thermosetting resin composition; and to a laminated sheet formed from the thermosetting resin composition.

BACKGROUND ART

Thermosetting resins, having a characteristic cross-linking structure to exhibit high heat resistance and dimensional stability, are widely used in fields requiring high reliability (e.g., electronic components). Particularly, a copper-clad laminated sheet or an interlayer dielectric material must have high adhesion-to-copper foil property for micro-wiring formation, or good processability for provision of, for example, holes through drilling or punching, so as to meet recent requirements for high-density technology. Also, in view of recent environmental problems, such a material must have heat resistance and flame retardancy superior to those of conventional ones, so as to meet requirements for mounting of electronic components by use of lead-free solder, or flame retardancy without use of a halogen-containing flame retardant. Meanwhile, from the viewpoints of the product safety and improvement of working environment, demand has arisen for a thermosetting resin composition which contains only less toxic components and does not generate, for example, toxic gas.

Bismaleimide compound, which is a thermosetting resin, exhibits good dielectric properties, flame retardancy, and heat resistance. However, since no known bismaleimide compound exhibits curing reactivity to epoxy resin, when such a compound is used as is in an epoxy-curing thermosetting resin, the resin exhibits insufficient heat resistance.

Therefore, there is disclosed a method in which an addition product of a bismaleimide compound and aminophenol is produced through kneading under heating, and the product is used as a curing agent in an epoxy-curing thermosetting resin composition (Patent Document 1 or 2). However, the method disclosed in Patent Document 1 or 2 produces an addition product of a bismaleimide compound and aminophenol at low yield. In addition, when a thermosetting resin composition containing the addition product is used in a copper-clad laminated sheet or an interlayer dielectric material, the sheet or material exhibits, for example, poor heat resistance and processability.

A variety of thermosetting resin compositions each containing melamine resin or a guanamine compound are already known (Patent Documents 3, 4, 5, 6, and 7).

Although melamine resin (thermosetting resin) or a guanamine compound exhibits good adhesion, flame retardancy, and heat resistance, the resin or the compound has poor solubility in an organic solvent and thus poses problems in that, for example, a thermosetting resin composition is difficult to prepare therefrom unless a highly toxic N-containing organic solvent (e.g., N,N-dimethylformamide) is used in a large amount, and, in addition, the thus-prepared composition exhibits poor storage stability.

Furthermore, a copper-clad laminated sheet or interlayer dielectric material formed from such a thermosetting resin composition poses a problem in terms of contamination of a chemical liquid (e.g., plating liquid) during production of, for example, an electronic component.

Thermosetting resin compositions each containing melamine resin or a thermosetting resin prepared through condensation of a guanamine compound by use of an aldehyde (e.g., formaldehyde) have improved solubility in an organic solvent. However, since those thermosetting resin compositions have low thermal decomposition temperature and generate toxic decomposition gas, the compositions may impair the working environment. In addition, such thermosetting resin compositions exhibits low heat resistance to recently required lead-free solder or insufficient copper cladding heat resistance. Since the thermosetting resin compositions exhibit insufficient adhesion-to-copper foil property, flexibility, or toughness for fine processing or wiring formation, the compositions may cause problems in that, for example, disconnection or exfoliation occurs in a circuit pattern, and cracking occurs during formation of, for example, holes through drilling or punching.

A methylolated guanamine resin is also disclosed (Patent Document 8). However, similar to the case of the aforementioned compositions, the resin poses problems in terms of, for example, heat resistance, adhesion, and processability.

Also, a thermosetting resin composition containing an addition product of a bismaleimide compound and aminobenzoic acid is disclosed (Patent Document 9). However, a cured product of the resin composition has low thermal decomposition temperature and exhibits low heat resistance to recently required lead-free solder or insufficient copper cladding heat resistance. The resin composition has poor solubility in an organic solvent and poses problems in terms of, for example, processability.

Patent Document 1: Japanese Patent Publication (kokoku) No. S63-034899
Patent Document 2: Japanese Patent Application Laid-Open (kokai) No. H06-032969
Patent Document 3: Japanese Patent Publication (kokoku) No. S62-046584
Patent Document 4: Japanese Patent Application Laid-Open (kokai) No. H10-067942
Patent Document 5: Japanese Patent Application Laid-Open (kokai) No. 2001-011672
Patent Document 6: Japanese Patent Application Laid-Open (kokai) No. H02-258820

Patent Document 7: Japanese Patent Application Laid-Open (kokai) No. H03-145476

Patent Document 8: Japanese Patent Publication (kokoku) No. S62-061051

Patent Document 9: Japanese Patent Publication (kokoku) No. H06-008342

DISCLOSURE OF THE INVENTION

Problems to be Solved by the Invention

In view of the foregoing, an object of the present invention is to provide a method for producing a curing agent having improved solubility in an organic solvent. Another object of the present invention is to provide a thermosetting resin composition which is well-balanced in all of adhesion-to-copper foil property, heat resistance, moisture resistance, flame retardancy, copper cladding heat resistance, and dielectric properties (relative dielectric constant and dielectric loss tangent), and which is useful for forming a printed wiring board for electronic devices. Still another object of the present invention is to provide a prepreg formed from the thermosetting resin composition. Yet another object of the present invention is to provide a laminated sheet formed from the thermosetting resin composition.

Means for Solving the Problems

In order to achieve the aforementioned objects, the present inventors have conducted extensive studies, and as a result have found that when, in an organic solvent, a maleimide compound having at least two N-substituted maleimido groups in a molecule thereof is reacted with an amine compound having an acidic substituent represented by a specific formula, the resultant organic-solvent-containing curing agent has good solubility in an organic solvent, and employment of the curing agent realizes production of a thermosetting resin composition, a prepreg, and a laminated sheet, which satisfies the aforementioned requirements and is useful for forming a printed wiring board for electronic devices. The present invention has been accomplished on the basis of this finding.

Accordingly, the present invention provides a method for producing a curing agent, a thermosetting resin composition, a prepreg, and a laminated sheet, which are described below.

1. A method for producing a curing agent having an acidic substituent and an unsaturated maleimido group, characterized by comprising reacting, in an organic solvent, a maleimide compound (a) having at least two N-substituted maleimido groups in a molecule thereof with an amine compound (b) having an acidic substituent represented by the following formula (I):

[F1]

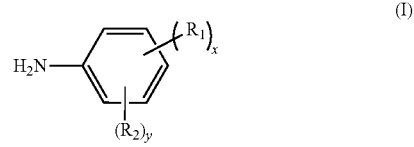

(wherein $R_1$, which is an acidic substituent, represents a hydroxyl group, a carboxyl group, or a sulfonic acid group; $R_2$ represents a hydrogen atom, a C1-C5 aliphatic hydrocarbon group, or a halogen atom; x is an integer from 1 to 5; y is an integer from 0 to 4; and the sum of x and y is 5).

2. A method for producing a curing agent having an acidic substituent and an unsaturated maleimido group as described in 1 above, wherein the curing agent having an acidic substituent and an unsaturated maleimido group is represented by the following formula (II):

[F2]

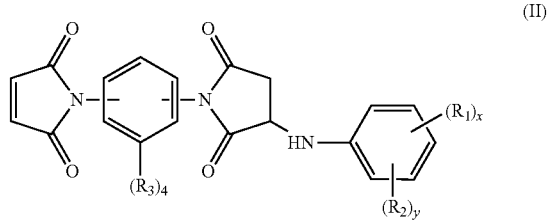

(wherein $R_1$, $R_2$, x, and y have the same meanings as defined above in formula (I), and $R_3$ represents a hydrogen atom, a C1-C5 aliphatic hydrocarbon group, or a halogen atom); or (III):

[F3]

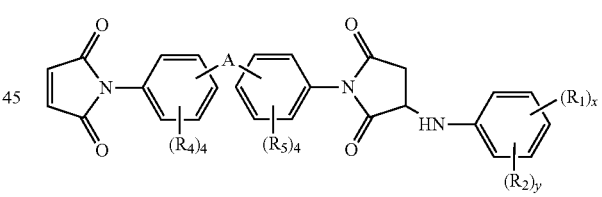

(wherein $R_1$, $R_2$, x, and y have the same meanings as defined above in formula (I); each of $R_4$ and $R_5$ represents a hydrogen atom, a C1-C5 aliphatic hydrocarbon group, or a halogen atom; A represents an alkylene group, an alkylidene group, an ether group, a sulfonyl group, or a group represented by the following formula (IV)):

[F4]

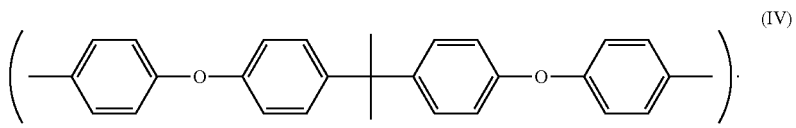

3. A thermosetting resin composition characterized by comprising a curing agent (A) having an acidic substituent and an unsaturated maleimido group produced through a method as recited in 1 or 2 above, and a compound (B) which is cured with the curing agent, wherein a cured product of the composition has a glass transition temperature of 200° C. or higher.

4. A thermosetting resin composition as described in 3 above, wherein the compound (B) which is cured with the curing agent is an amine compound having at least two primary amino groups in a molecule thereof.

5. A thermosetting resin composition as described in 3 above, wherein the compound (B) which is cured with the curing agent is a 6-substituted guanamine compound represented by the following formula (V):

[F5]

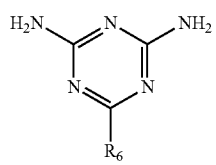

(wherein $R_6$ represents a phenyl group, a methyl group, an allyl group, a butyl group, a methoxy group, or a benzyloxy group), and the composition further contains a carboxyl-group-containing acidic compound (C) having an acid dissociation constant (pKa) of 4.05 or more in an infinitely diluted aqueous solution at 25° C.

6. A thermosetting resin composition as described in any of 3 to 5 above, which further contains an epoxy resin (D) having at least two epoxy groups in a molecule thereof.

7. A thermosetting resin composition as described in any of 3 to 6 above, which further contains an inorganic filler (E).

8. A prepreg produced by impregnating or coating a base with a thermosetting resin composition as recited in any of 3 to 7 above, and B-staging the composition.

9. A laminated sheet produced through laminate molding of a prepreg as recited in 8 above.

Effects of the Invention

The curing agent produced through the method of the present invention has good solubility in an organic solvent and can provide a thermosetting resin composition exhibiting excellent adhesion-to-metal foil property, heat resistance, moisture resistance, flame retardancy, and copper cladding heat resistance, and low dielectric properties and low dielectric loss tangent.

Therefore, according to the present invention, employment of the thermosetting resin composition realizes provision of, for example, a prepreg or laminated sheet exhibiting excellent performance.

BEST MODES FOR CARRYING OUT THE INVENTION

The present invention will next be described in detail. The curing agent produced through the method of the present invention contains an organic solvent. The thermosetting resin serving as a component (B) may be a monomer or an oligomer.

In the method for producing a curing agent of the present invention, firstly, a maleimide compound (a) having at least two N-substituted maleimido groups in a molecule thereof is reacted with an amine compound (b) having an acidic substituent represented by formula (I) in an organic solvent.

Examples of the component (a) (i.e., a maleimide compound having at least two N-substituted maleimido groups in a molecule thereof) include bis(4-maleimidophenyl)methane, bis(4-maleimidophenyl)ether, bis(4-maleimidophenyl) sulfone, 3,3-dimethyl-5,5-diethyl-4,4-diphenylmethane bismaleimide, 4-methyl-1,3-phenylene bismaleimide, m-phenylene bismaleimide, and 2,2-bis(4-(4-maleimidophenoxy) phenyl)propane. Of these, preferred are bis(4-maleimidophenyl)methane, m-phenylene bismaleimide, and bis(4-maleimidophenyl) sulfone, which provide high percent reaction and can attain high heat resistance. More preferred are m-phenylene bismaleimide and bis(4-maleimidophenyl) methane, from the viewpoint of inexpensiveness. Particularly preferred is bis(4-maleimidophenyl)methane, from the viewpoint of solubility in a solvent.

The component (b) (i.e., an amine compound represented by the following formula (I)) has an acidic substituent selected from among a hydroxyl group, a carboxyl group, and a sulfonic acid group.

[F6]

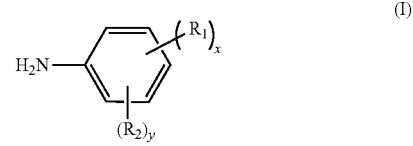

(In formula (I), $R_1$, which is an acidic substituent, represents a hydroxyl group, a carboxyl group, or a sulfonic acid group; $R_2$ represents a hydrogen atom, a C1-C5 aliphatic hydrocarbon group, or a halogen atom; x is an integer from 1 to 5; y is an integer from 0 to 4; and the sum of x and y is 5.)

Examples of the amine compound (b) represented by formula (I) include m-aminophenol, p-aminophenol, o-aminophenol, p-aminobenzoic acid, m-aminobenzoic acid, o-aminobenzoic acid, o-aminobenzenesulfonic acid, m-aminobenzenesulfonic acid, p-aminobenzenesulfonic acid, 3,5-dihydroxyaniline, and 3,5-dicarboxyaniline. Of these, preferred are m-aminophenol, p-aminophenol, p-aminobenzoic acid, m-aminobenzoic acid, and 3,5-dihydroxyaniline, from the viewpoints of solubility and synthetic yield. More preferred are m-aminophenol and p-aminophenol, from the viewpoint of heat resistance. Particularly preferred is m-aminophenol, from the viewpoint of low toxicity.

No particular limitation is imposed on the organic solvent employed in the aforementioned reaction. Examples of employable organic solvents include alcohol solvents such as ethanol, propanol, butanol, methyl cellosolve, butyl cellosolve, and propylene glycol monomethyl ether; ketone solvents such as acetone, methyl ethyl ketone, methyl isobutyl ketone, and cyclohexanone; ether solvents such as tetrahydrofuran; aromatic solvents such as toluene, xylene, and mesitylene; nitrogen-containing solvents such as dimethylformamide, dimethylacetamide, and N-methylpyrrolidone; and sulfur-containing solvents such as dimethyl sulfoxide. These solvents may be employed singly or in combination of two or more species.

Of these solvents, preferred are cyclohexanone, propylene glycol monomethyl ether, and methyl cellosolve, from the viewpoint of solubility. More preferred are cyclohexanone and propylene glycol monomethyl ether, from the viewpoint of low toxicity. Particularly preferred is propylene glycol monomethyl ether, which exhibits high volatility and is less likely to remain during production of a prepreg.

Regarding the amounts of the maleimide compound (component (a)) and the amine compound (component (b)) employed, the ratio of the maleimido group equivalent ($T_a$) of the maleimide compound (a) to the —NH$_2$ group equivalent ($T_b$) of the component (b); i.e., ($T_a/T_b$), is preferably 1.0 to 10.0, more preferably 2.0 to 10.0. When the ratio ($T_a/T_b$) is 1.0 or more, the resultant thermosetting resin composition exhibits heat resistance, whereas when the ratio ($T_a/T_b$) is 10.0 or less, the curing agent has sufficient solubility in an organic solvent, and the resultant thermosetting resin composition exhibits heat resistance.

The amount of the organic solvent employed is preferably 10 to 1,000 parts by mass, more preferably 100 to 500 parts by mass, particularly preferably 200 to 500 parts by mass, on the basis of the total amount of the components (a) and (b) (100 parts by mass). When the amount of the organic solvent is less than 10 parts by mass, the curing agent may have insufficient solubility in an organic solvent, whereas when the amount of the organic solvent exceeds 1,000 parts by mass, synthesis may require a long period of time.

The temperature of reaction between the components (a) and (b) is preferably 50 to 200° C., particularly preferably 100 to 160° C. The reaction time is preferably 0.1 to 10 hours, particularly preferably 1 to 8 hours. The curing agent having an acidic substituent and an unsaturated maleimido group is produced by, for example, reacting the component (a) with the component (b) in an organic solvent under stirring with optional heating or temperature maintenance.

If necessary, a reaction catalyst may be employed in this reaction. Examples of the reaction catalyst include amines such as triethylamine, pyridine, and tributylamine; imidazoles such as methylimidazole and phenylimidazole; and phosphorus-containing catalysts such as triphenylphosphine. These catalysts may be employed singly or in combination of two or more species.

Examples of the product produced through reaction between the components (a) and (b) include products represented by the following formulas (II):

[F7]

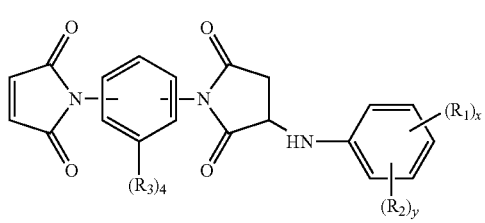

(II)

(wherein $R_1$, $R_2$, x, and y have the same meanings as defined above in formula (I), and $R_3$ represents a hydrogen atom, a C1-C5 aliphatic hydrocarbon group, or a halogen atom.), or the following formulas (III):

[F8]

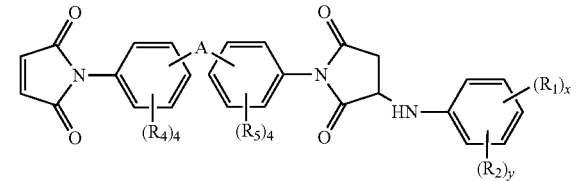

(III)

(wherein $R_1$, $R_2$, x, and y have the same meanings as defined above in formula (I); each of $R_4$ and $R_5$ represents a hydrogen atom, a C1-C5 aliphatic hydrocarbon group, or a halogen atom; A represents an alkylene group, an alkylidene group, an ether group, a sulfonyl group, or a group represented by the following formula (IV).)

[F9]

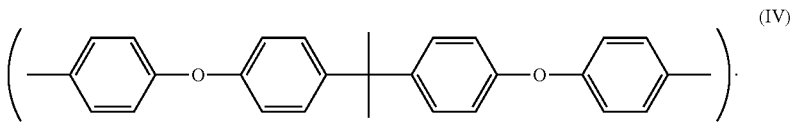

(IV)

A characteristic feature of the thermosetting resin composition of the present invention resides in that the composition contains the curing agent (A) produced through the aforementioned method and a compound (B) which is cured with the curing agent, and that a cured product of the composition has a glass transition temperature of 200° C. or higher.

Since the thermosetting resin composition of the present invention attains a glass transition temperature of 200° C. or higher, the composition realizes good solder heat resistance, and good processability for production of, for example, electronic components.

The component (B) (i.e., a compound which is cured with the curing agent) is preferably an amine compound having at least two primary amino groups in a molecule thereof.

Examples of the amine compound having at least two primary amino groups in a molecule thereof include aromatic amines such as m-phenylenediamine, p-phenylenediamine, 3,5-diaminophenol, 3,5-diaminobenzoic acid, 4,4'-diaminodiphenylmethane, 4,4'-diaminodiphenyl ether, 4,4'-diaminodiphenyl sulfone, 3,3'-diaminodiphenyl sulfone, 4,4'-diaminodiphenyl ketone, benzidine, 3,3'-dihydroxybenzidine, 2,2-bis(3-amino-4-hydroxyphenyl)propane, 3,3-dimethyl-5,5-diethyl-4,4-diphenylmethanediamine, 4-methyl-1,3-phenylenediamine, 2,2-bis(4-aminophenyl)propane, 2,2-bis(4-(4-aminophenoxy)phenyl)propane, 1,3-bis(3-aminophenoxy)benzene, 1,3-bis(4-aminophenoxy)benzene, 1,4-bis(4-aminophenoxy)benzene, 4,4'-bis(4-aminophenoxy)biphenyl, bis(4-(4-aminophenoxy)phenyl) sulfone, bis (4-(3-aminophenoxy)phenyl) sulfone, and 9,9-bis(4-aminophenyl)fluorene; aliphatic amines such as ethylenediamine, n-butylenediamine, n-hexamethylenediamine, and trimethylhexamethylenediamine; and guanamine compounds such as melamine, benzoguanamine, acetoguanamine, and 2,4-diamino-6-vinyl-s-triazine.

Of these, the component (B) is preferably an aromatic amine or guanamine compound which provides high percent reaction and can attain higher heat resistance. From the viewpoints of low dielectric properties and thermal stability during storage of a prepreg, the component (B) is more preferably a 6-substituted guanamine compound represented by the following formula (V):

[F10]

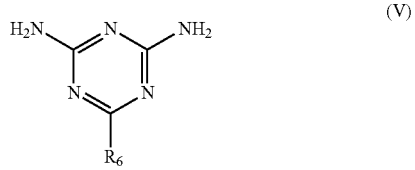

(V)

(wherein $R_6$ represents a phenyl group, a methyl group, an allyl group, a butyl group, a methoxy group, or a benzyloxy group) (hereinafter may be referred to simply as a "guanamine compound").

Examples of such a 6-substituted guanamine compound include benzoguanamine (2,4-diamino-6-phenyl-s-triazine), acetoguanamine (2,4-diamino-6-methyl-s-triazine), and 2,4-diamino-6-vinyl-s-triazine. From the viewpoint of cost, benzoguanamine is particularly preferred.

The thermosetting resin composition of the present invention preferably contains, in addition to the component (A) (i.e., the curing agent) and the component (B) (i.e., a 6-substituted guanamine compound represented by formula (V)), a component (C); i.e., a carboxyl-group-containing acidic compound having an acid dissociation constant (pKa) of 4.05 or more in an infinitely diluted aqueous solution at 25° C.

Examples of the component (C) (i.e., carboxyl-group-containing acidic compound having an acid dissociation constant (pKa) of 4.05 or more in an infinitely diluted aqueous solution at 25° C.) include acrylic acid, adipic acid, azelaic acid, (o-, m-, or p-)anisic acid, 4-aminobutyric acid, isobutyric acid, isovaleric acid, valeric acid, glutaric acid, acetic acid, cyclohexanecarboxylic acid, 2-naphthoic acid, (o-, m-, or p-)hydroxybenzoic acid, pimelic acid, phenylacetic acid, p-fluorobenzoic acid, propionic acid, hexanoic acid, heptanoic acid, butyric acid, and levulinic acid.

Of these, preferred are acrylic acid, adipic acid, (o-, m-, or p-)anisic acid, isobutyric acid, glutaric acid, acetic acid, cyclohexanecarboxylic acid, (o-, m-, or p-) hydroxybenzoic acid, phenylacetic acid, p-fluorobenzoic acid, propionic acid, hexanoic acid, heptanoic acid, and butyric acid, in which the guanamine compound has high solubility, and which can attain higher heat resistance. More preferred is (o-, m- or p-)hydroxybenzoic acid, from the viewpoint of excellent flame retardancy. Particularly preferred is p-hydroxybenzoic acid, from the viewpoints of inexpensiveness and excellent adhesion-to-copper foil property.

As used herein, "acid dissociation constant (pKa) in an infinitely diluted aqueous solution at 25° C." is cited from "*Kagaku Binran* (Chemical Handbook)" (revised version 4, Basic Edition II, page 317, Maruzen Co., Ltd., published in 1993).

The thermosetting resin composition of the present invention preferably contains, in addition to the components (A), (B), and (C), a component (D); i.e., an epoxy resin having at least two epoxy groups in a molecule thereof.

No particular limitation is imposed on the component (D), so long as it is an epoxy resin having at least two epoxy groups in a molecule thereof. Examples of employable epoxy resins include glycidyl ether epoxy resins, glycidyl amine epoxy resins, and glycidyl ester epoxy resins, such as bisphenol A epoxy resin, bisphenol F epoxy resin, biphenyl epoxy resin, novolak epoxy resin, polyfunctional phenol epoxy resin, naphthalene epoxy resin, alicyclic epoxy resin, and alcohol epoxy resin. These epoxy resins may be employed singly or in combination of two or more species.

Of these epoxy resins (component (D)), preferred are, for example, bisphenol F epoxy resin, dicyclopentadiene epoxy resin, bisphenol A novolak epoxy resin, biphenyl epoxy resin, biphenyl aralkyl epoxy resin, phenol novolak epoxy resin, and cresol novolak epoxy resin, from the viewpoints of dielectric properties, heat resistance, moisture resistance, and adhesion-to-copper foil property. More preferred are bisphenol F epoxy resin, biphenyl aralkyl epoxy resin, biphenyl epoxy resin, phenol novolak epoxy resin, and cresol novolak epoxy resin, from the viewpoints of flame retardancy and moldability. Particularly preferred are phenol novolak epoxy resin and cresol novolak epoxy resin, from the viewpoint of inexpensiveness.

When the thermosetting resin composition of the present invention contains the component (D), an epoxy resin curing agent or an epoxy resin curing accelerator may be employed in combination. Examples of such an agent include acid anhydrides such as maleic anhydride and maleic anhydride copolymer; amine compounds such as dicyanodiamide; and phenolic compounds such as phenol novolak and cresol novolak. Of these, preferred are phenolic compounds such as phenol novolak and cresol novolak, which attain good heat resistance. Particularly preferred is cresol novolak phenolic resin, which improves flame retardancy or adhesion.

Examples of the epoxy resin curing accelerator include imidazoles and derivatives thereof, tertiary amines, and quaternary ammonium salts.

In the thermosetting resin composition containing the aforementioned components (A) to (D), when the sum of the solid content of the component (A) and the amounts of the components (B), (C), and (D) is 100 parts by mass, the solid content of the component (A) and the respective amounts of the components (B), (C), and (D) are as follows.

The solid content of the component (A) is preferably 1 to 97 parts by mass, more preferably 10 to 88 parts by mass, particularly preferably 20 to 78 parts by mass. When the solid content of the component (A) is 1 part by mass or more, sufficient flame retardancy, adhesion, and flexibility are attained, whereas when the solid content of the component (A) is 97 parts by mass or less, reduction in heat resistance is prevented.

The amount of the component (B) is preferably 1 to 50 parts by mass, more preferably 1 to 30 parts by mass, particularly preferably 1 to 20 parts by mass. When the amount of the component (B) is 1 part by mass or more, sufficient flame retardancy, adhesion, and dielectric properties are attained, whereas when the amount of the component (B) is 50 parts by mass or less, reduction in heat resistance is prevented.

The amount of the component (C) is preferably 1 to 50 parts by mass, more preferably 1 to 30 parts by mass, particularly preferably 1 to 20 parts by mass. When the amount of the component (C) is 1 part by mass or more, sufficient solubility is attained, whereas when the amount of the component (C) is 50 parts by mass or less, reduction in heat resistance is prevented.

The amount of the component (D) is preferably 1 to 97 parts by mass, more preferably 10 to 88 parts by mass, particularly preferably 20 to 78 parts by mass. When the amount of the component (D) is 1 part by mass or more, sufficient flame retardancy, adhesion, and flexibility are attained, whereas when the amount of the component (D) is 97 parts by mass or less, reduction in heat resistance is prevented.

The amount of the component (D) (parts by mass) corresponds to the total amount (parts by mass) of the epoxy resin and an optionally added epoxy resin curing agent or epoxy resin curing accelerator.

The thermosetting resin composition of the present invention may optionally contain an inorganic filler (i.e., component (E)) for the purpose of, for example, improvement of properties (e.g., strength and durability) or price reduction. Examples of the inorganic filler include silica, mica, talc, short glass fiber, fine glass powder, hollow glass, antimony trioxide, calcium carbonate, quartz powder, aluminum hydroxide, and magnesium hydroxide. Of these, preferred are silica, aluminum hydroxide, and magnesium hydroxide, from the viewpoints of dielectric properties, heat resistance, and flame retardancy. More preferred are silica and aluminum hydroxide, from the viewpoint of inexpensiveness.

The amount of the inorganic filler (component (E)) employed is preferably 0 to 300 parts by mass, more preferably 20 to 200 parts by mass, particularly preferably 20 to 150 parts by mass, on the basis of the sum (100 parts by mass) of the solid content of the component (A) and the amounts of the components (B), (C), and (D). When the amount of the component (E) exceeds 300 parts by mass, moldability or adhesion tends to be impaired.

The thermosetting resin composition of the present invention may also contain, for example, any known thermoplastic resin, elastomer, flame retardant, or filler, so long as the objects of the present invention are not impeded.

Examples of the thermoplastic resin include polytetrafluoroethylene, polyethylene, polypropylene, polystyrene, polyphenylene ether resin, phenoxy resin, polycarbonate resin, polyester resin, polyamide resin, polyimide resin, xylene resin, petroleum resin, and silicone resin.

Examples of the elastomer include polybutadiene, polyacrylonitrile, epoxy-modified polybutadiene, maleic-anhydride-modified polybutadiene, phenol-modified polybutadiene, and carboxy-modified polyacrylonitrile.

Examples of the flame retardant include halogen (bromine Or chlorine)-containing flame retardants; phosphorus-containing flame retardants such as triphenyl phosphate, tricresyl phosphate, trisdichloropropyl phosphate, phosphazene, and red phosphorus; and inorganic flame retardants such as antimony trioxide, aluminum hydroxide, and magnesium hydroxide. Of these flame retardants, non-halogen flame retardants (e.g., phosphorus-containing flame retardants or inorganic flame retardants) are preferred from the environmental viewpoint, since the thermosetting resin composition of the present invention is advantageous in its high flame retardant effect. Particularly preferably, a phosphorus-containing flame retardant and an inorganic flame retardant (e.g., aluminum hydroxide) are employed in combination, from the viewpoints of inexpensiveness, flame retardancy, and balance between flame retardancy and other properties (e.g., heat resistance).

Examples of the filler include silicone powder and powder of an organic substance (e.g., polytetrafluoroethylene, polyethylene, polypropylene, polystyrene, or polyphenylene ether).

In the present invention, the thermosetting resin composition may optionally contain an additive. Examples of the additive include, but are not particularly limited to, a UV absorbent (e.g., benzotriazole), an antioxidant (e.g., hindered phenol or styrenated phenol), a photopolymerization initiator (e.g., benzophenone, benzylketal, or thioxanthone), a fluorescent whitening agent (e.g., a stilbene derivative), a urea compound (e.g., urea silane), and an adhesion-improving agent (e.g., a silane coupling agent).

The prepreg of the present invention is produced by impregnating or coating a base with the aforementioned thermosetting resin composition, followed by B-staging of the composition. Specifically, the prepreg of the present invention may be produced by impregnating or coating a base with the thermosetting resin composition of the present invention, followed by semi-curing (B-staging) of the composition through, for example, heating. The prepreg of the present invention will next be described in detail.

The base employed in the prepreg of the present invention may be a well-known base employed in a variety of laminated sheets for electrical insulating material. Examples of the material of the base include fiber of an inorganic substance (e.g., E-glass, D-glass, S-glass, or Q-glass), fiber of an organic substance (e.g., polyimide, polyester, or polytetrafluoroethylene), and mixtures thereof. Such a base is in the form of, for example, woven fabric, nonwoven fabric, roving, chopped strand mat, or surfacing mat. The material or form of the base employed is selected in consideration of the use or performance of a target molded product. The aforementioned materials (or forms) may be employed singly, or, if necessary, two or more of the materials (or forms) may be employed in combination.

No particular limitation is imposed on the thickness of the base employed, and the thickness may be, for example, about 0.03 to about 0.5 mm. Preferably, the base is subjected to surface treatment with, for example, a silane coupling agent, or to mechanical fibrillation treatment, from the viewpoints of heat resistance, moisture resistance, and processability. The prepreg of the present invention may be produced through the following procedure: the base is impregnated or coated with the resin composition so that the resin content of a prepreg is 20 to 90 mass % after drying, and subsequently drying is generally carried out under heating at 100 to 200° C. for 1 to 30 minutes for semi-curing (B-staging) of the composition.

The laminated sheet of the present invention is produced through laminate molding of the aforementioned prepreg of the present invention. Specifically, the laminated sheet may be produced through the following procedure: for example, 1 to 20 prepregs of the present invention are laminated, and a metal foil (e.g., copper foil or aluminum foil) is provided on one surface or both surfaces of the laminated product, followed by laminate molding. No particular limitation is imposed on the metal foil, so long as it is employed in electrical insulating materials. Laminate molding may be carried out through a technique for forming, for example, a laminated sheet for electrical insulating material or a multi-layer sheet. Specifically, laminate molding may be performed by means of, for example, a multi-platen press, a multi-platen vacuum press, a continuous molding machine, or an autoclave molding machine under the following conditions: temperature: 100 to 250° C., pressure: 0.2 to 10 MPa, and heating time: 0.1 to 5 hours. A multi-layer sheet may be produced through laminating of the prepreg of the present invention together with an inner-layer wiring board.

EXAMPLES

The present invention will next be described in more detail by way of examples, which should not be construed as limiting the invention thereto.

Characteristics of the copper-clad laminated sheets produced in the Examples described hereinbelow were determined and evaluated as follows.

(1) Evaluation of Adhesion-to-Copper Foil Property (Copper Foil Peeling Strength)

Evaluation substrates were prepared from each copper-clad laminated sheet by immersing the sheet in a copper etchant so that copper foil remained in the form of a slip (width: 1 cm). The adhesion-to-copper foil property of each evaluation substrate was evaluated by measuring the peeling strength of the Cu slip portion by means of Autograph AG-100C [product of Shimadzu Corporation].

(2) Measurement of Glass Transition Temperature (Tg)

Copper-foil-removed evaluation substrates (5 mm×5 mm) were prepared from each copper-clad laminated sheet by immersing the sheet in a copper etchant. Glass transition temperature was measured by means of a TMA tester [TMA 2940, product of Du Pont] on the basis of the thermal expansion properties of each evaluation substrate.

(3) Evaluation of Solder Heat Resistance

Copper-foil-removed evaluation substrates (5 cm×5 cm) were prepared from each copper-clad laminated sheet by immersing the sheet in a copper etchant. Each evaluation substrate was allowed to stand for four hours at 121° C. and 0.2 MPa in a pressure cooker tester [product of Hirayama Manufacturing Corporation]. Thereafter, the substrate was immersed in a solder bath at 288° C. for 20 seconds. Solder heat resistance was evaluated through observation of the appearance of the thus-immersed substrate.

(4) Evaluation of Copper Cladding Heat Resistance (T-288)

Evaluation substrates (5 mm×5 mm) were prepared from each copper-clad laminated sheet. Copper cladding heat resistance was evaluated by means of a TMA tester [TMA 2940, product of Du Pont] on the basis of the time required for any blister to occur in each evaluation substrate at 288° C.

(5) Determination of Hygroscopicity (Percent Water Absorption)

Copper-foil-removed evaluation substrates were prepared from each copper-clad laminated sheet by immersing the sheet in a copper etchant. Each evaluation substrate was allowed to stand for four hours at 121° C. and 0.2 MPa in a pressure cooker tester [product of Hirayama Manufacturing Corporation]. Subsequently the percent water absorption of the substrate was measured.

(6) Evaluation of Flame Retardancy

Each copper-clad laminated sheet was immersed in a copper etchant for removal of copper foil, and evaluation substrates (length: 127 mm, width: 12.7 mm) were cut out of the copper-foil-removed sheet, followed by evaluation of flame retardancy according to the UL 94 test method (V method).

(7) Measurement of Relative Dielectric Constant and Dielectric Loss Tangent

Copper-foil-removed evaluation substrates were prepared from each copper-clad laminated sheet by immersing the sheet in a copper etchant. The relative dielectric constant and dielectric loss tangent of each evaluation substrate were measured by means of a relative dielectric constant measuring apparatus (HP 4291B, product of Hewlett Packard) at a frequency of 1 GHz.

Production Example 1

Production of Curing Agent (A-1)

Bis(4-maleimidophenyl)methane (358.00 g), m-aminophenol (54.50 g), and an organic solvent (propylene glycol monomethyl ether) (412.50 g) were added to a reactor which can heat and cool the content (capacity: 2 L) and which was equipped with a thermometer, a stirrer, a reflux cooling tube, and a moisture meter, and reaction was carried out for five hours under reflux, to thereby yield a curing agent (A-1) containing the organic solvent.

Production Example 2

Production of Curing Agent (A-2)

Bis(4-maleimidophenyl)methane (358.00 g), p-aminophenol (54.50 g), and an organic solvent (propylene glycol monomethyl ether) (412.50 g) were added to a reactor which can heat and cool the content (capacity: 2 L) and which was equipped with a thermometer, a stirrer, a reflux cooling tube, and a moisture meter, and reaction was carried out for five hours under reflux, to thereby yield a curing agent (A-2) containing the organic solvent.

Production Example 3

Production of Curing Agent (A-3)

Bis(4-maleimidophenyl)methane (358.00 g), p-aminobenzoic acid (68.50 g), and an organic solvent (N,N-dimethylacetamide) (426.50 g) were added to a reactor which can heat and cool the content (capacity: 2 L) and which was equipped with a thermometer, a stirrer, a reflux cooling tube, and a moisture meter, and reaction was carried out at 140° C. for five hours, to thereby yield a curing agent (A-3) containing the organic solvent.

Production Example 4

Production of Curing Agent (A-4)

m-Phenylene bismaleimide (268.00 g), m-aminophenol (54.50 g), and an organic solvent (N,N-dimethylacetamide) (322.50 g) were added to a reactor which can heat and cool the content (capacity: 1 L) and which was equipped with a thermometer, a stirrer, a reflux cooling tube, and a moisture meter, and reaction was carried out at 140° C. for five hours, to thereby yield a curing agent (A-4) containing the organic solvent.

Production Example 5

Production of Curing Agent (A-5)

Bis(4-maleimidophenyl) sulfone (408.0 g), p-aminophenol (54.5 g), and N,N-dimethylacetamide (462.5 g) were added to a reactor which can heat and cool the content (capacity: 2 L) and which was equipped with a thermometer, a stirrer, a reflux cooling tube, and a moisture meter, and reaction was carried out at 100° C. for two hours, to thereby yield a solution of a curing agent (A-5) containing the organic solvent.

Production Example 6

Production of Curing Agent (A-6)

Bis(4-maleimidophenyl)ether (360.0 g), p-aminophenol (54.5 g), and N,N-dimethylacetamide (414.5 g) were added to a reactor which can heat and cool the content (capacity: 2 L) and which was equipped with a thermometer, a stirrer, a reflux cooling tube, and a moisture meter, and reaction was carried out at 100° C. for two hours, to thereby yield a solution of a curing agent (A-6) containing the organic solvent.

Production Example 7

Production of Curing Agent (A-7)

2,2'-Bis[4-(4-maleimidophenoxy)phenyl]propane (570.0 g), p-aminophenol (54.5 g), and propylene glycol monomethyl ether (624.5 g) were added to a reactor which can heat and cool the content (capacity: 2 L) and which was equipped with a thermometer, a stirrer, a reflux cooling tube, and a moisture meter, and reaction was carried out at 120° C. for two hours, to thereby yield a solution of a curing agent (A-7) containing the organic solvent.

Production Example 8

Production of Curing Agent (A-8)

4-Methyl-1,3-phenylene bismaleimide (282.0 g), p-aminophenol (54.5 g), and propylene glycol monomethyl ether (336.5 g) were added to a reactor which can heat and cool the content (capacity: 2 L) and which was equipped with a thermometer, a stirrer, a reflux cooling tube, and a moisture meter, and reaction was carried out at 120° C. for two hours, to thereby yield a solution of a curing agent (A-8) containing the organic solvent.

Comparative Production Example 1

Production of Curing Agent (A-9)

With reference to Examples described in Patent Document 1, bis(4-maleimidophenyl)methane (358.00 g) and m-aminophenol (54.50 g) were added to a kneader (capacity: 1 L) equipped with a steam heating apparatus, and the mixture was kneaded under heating at 135 to 140° C. for 15 minutes, followed by cooling and grinding, to thereby yield powder of a curing agent (A-9). Since no organic solvent was employed in Comparative Production Example 1, the curing agent (A-9) does not correspond to the curing agent produced through the production method of the present invention.

Comparative Production Example 2

Production of Curing Agent (A-10)

With reference to Examples described in Patent Document 9, bis(4-maleimidophenyl)methane (358.00 g) and m-aminobenzoic acid (68.50 g) were added to a kneader (capacity: 1 L) equipped with a steam heating apparatus, and the mixture was kneaded under heating at 135 to 140° C. for 15 minutes, followed by cooling and grinding, to thereby yield powder of a curing agent (A-10). Since no organic solvent was employed in Comparative Production Example 2, the curing agent (A-10) does not correspond to the curing agent produced through the production method of the present invention.

Examples 1 to 10 and Comparative Examples 1 to 6

A uniform varnish (solid content: 70 mass %) was prepared by mixing a component (A) (i.e., a curing agent produced in each of Production Examples 1 to 8 and Comparative Production Examples 1 and 2), a component (B) (i.e., benzoguanamine serving as a 6-substituted guanamine compound), a component (C) (i.e., a carboxyl-group-containing acidic compound), a component (D) (i.e., phenol novolak resin serving as an epoxy resin or an epoxy curing agent), and a component (E) (i.e., aluminum hydroxide and ground silica serving as inorganic fillers) in proportions (parts by mass) shown in Tables 1 to 3 by use of methyl ethyl ketone serving as a dilution solvent.

Subsequently, E-glass cloth (thickness: 0.2 mm) was impregnated or coated with the above-prepared varnish, and drying was carried out under heating at 160° C. for 10 minutes, to thereby yield a prepreg having a solid content of 55 mass %. Four prepregs were laminated together, and electrolytic copper foils (thickness: 18 μm) were provided on the top and bottom surfaces of the thus-laminated product, followed by pressing at 2.45 MPa and 185° C. for 90 minutes, to thereby yield a copper-clad laminated sheet.

The performance of the thus-yielded copper-clad laminated sheet was evaluated by determining (1) adhesion-to-copper foil property (copper foil peeling strength), (2) glass transition temperature, (3) solder heat resistance, (4) copper cladding heat resistance (T-288), (5) hygroscopicity (percent water absorption), (6) flame retardancy, (7) relative dielectric constant (1 GHz), and (8) dielectric loss tangent (1 GHz) as described above. The results of determination (evaluation) are shown in Tables 1 to 3.

TABLE 1

|  | Ex. 1 | Ex. 2 | Ex. 3 | Ex. 4 | Ex. 5 | Ex. 6 |
| --- | --- | --- | --- | --- | --- | --- |
| Thermosetting resin composition (parts by mass) | | | | | | |
| (A) Curing agent: | | | | | | |
| A-1 | 40 | | | | 40 | |
| A-2 | | 40 | | | | 40 |
| A-3 | | | 40 | | | |
| A-4 | | | | 40 | | |
| (B) 6-Substituted guanamine compound | 10 | 10 | 10 | 10 | 10 | 10 |

TABLE 1-continued

|  | Ex. 1 | Ex. 2 | Ex. 3 | Ex. 4 | Ex. 5 | Ex. 6 |
|---|---|---|---|---|---|---|
| (C) Carboxyl-group-containing acidic compound | | | | | | |
| C1: p-Hydroxybenzoic acid | 7 | 7 | 7 | 7 | 7 | 7 |
| C2: Benzoic acid | | | | | | |
| (D) Epoxy resin | | | | | | |
| D1: Phenol novolak epoxy resin | 43 | 43 | 43 | 43 | | |
| D2: Cresol novolak epoxy resin | | | | | 33 | 33 |
| (Epoxy curing agent) | | | | | | |
| Cresol novolak phenolic resin | | | | | 10 | 10 |
| (E) Inorganic filler | | | | | | |
| Ground silica | 10 | 10 | 10 | 10 | 10 | 10 |
| Aluminum hydroxide | 80 | 80 | 80 | 80 | 80 | 80 |
| Results of determination (evaluation) | | | | | | |
| (1) Adhesion-to-copper foil property (copper foil peeling strength: kN/m) | 1.60 | 1.65 | 1.69 | 1.62 | 1.61 | 1.60 |
| (2) Glass transition temperature (Tg: °C.) | 230 | 225 | 228 | 230 | 230 | 235 |
| (3) Solder heat resistance | Good | Good | Good | Good | Good | Good |
| (4) Copper cladding heat resistance (T-288: min) | >60 | >60 | >60 | >60 | >60 | >60 |
| (5) Hygroscopicity (percent water absorption: %) | 0.5 | 0.5 | 0.5 | 0.5 | 0.5 | 0.5 |
| (6) Flame retardancy | V-0 | V-0 | V-0 | V-0 | V-0 | V-0 |
| (7) Relative dielectric constant (1 GHz) | 4.5 | 4.5 | 4.5 | 4.5 | 4.6 | 4.5 |
| (8) Dielectric loss tangent (1 GHz) | 0.005 | 0.004 | 0.005 | 0.006 | 0.006 | 0.006 |

TABLE 2

|  | Ex. 7 | Ex. 8 | Ex. 9 | Ex. 10 |
|---|---|---|---|---|
| Thermosetting resin composition (parts by mass) | | | | |
| (A) Curing agent: A-5 | 40 | | | |
| A-6 | | 40 | | |
| A-7 | | | 40 | |
| A-8 | | | | 40 |
| (B) 6-Substituted guanamine compound | 10 | 10 | 10 | 10 |
| (C) Carboxyl-group-containing acidic compound | | | | |
| C1: p-Hydroxybenzoic acid | 7 | 7 | 7 | 7 |
| C2: Benzoic acid | | | | |
| (D) Epoxy resin | | | | |
| D1: Phenol novolak epoxy resin | 43 | 43 | 43 | 43 |
| D2: Cresol novolak epoxy resin | | | | |
| (Epoxy curing agent) | | | | |
| Cresol novolak phenolic resin | | | | |
| (E) Inorganic filler | | | | |
| Ground silica | 10 | 10 | 10 | 10 |
| Aluminum hydroxide | 80 | 80 | 80 | 80 |
| Results of determination (evaluation) | | | | |
| (1) Adhesion-to-copper foil property (copper foil peeling strength: kN/m) | 1.60 | 1.65 | 1.69 | 1.62 |
| (2) Glass transition temperature (Tg: °C.) | 230 | 225 | 228 | 230 |
| (3) Solder heat resistance | Good | Good | Good | Good |
| (4) Copper cladding heat resistance (T-288: min) | >60 | >60 | >60 | >60 |
| (5) Hygroscopicity (percent water absorption: %) | 0.5 | 0.5 | 0.5 | 0.5 |
| (6) Flame retardancy | V-0 | V-0 | V-0 | V-0 |
| (7) Relative dielectric constant (1 GHz) | 4.4 | 4.3 | 4.2 | 4.3 |
| (8) Dielectric loss tangent (1 GHz) | 0.004 | 0.003 | 0.004 | 0.005 |

TABLE 3

|  | Comp. Ex. 1 | Comp. Ex. 2 | Comp. Ex. 3 | Comp. Ex. 4 | Comp. Ex. 5 | Comp. Ex. 6 |
|---|---|---|---|---|---|---|
| Thermosetting resin composition (parts by mass) | | | | | | |
| (A) Curing agent: | | | | | | |
| A-1 | | | 40 | | 40 | |
| A-9 | 40 | | | 40 | | 40 |
| A-10 | | 40 | | | | |
| (B) 6-Substituted guanamine compound | 10 | 10 | | | 10 | 10 |
| (C) Carboxyl-group-containing acidic compound | | | | | | |
| C1: p-Hydroxybenzoic acid | 7 | 7 | | | | |
| C2: Benzoic acid | | | | | 7 | 7 |
| (D) Epoxy resin | | | | | | |
| D1: Phenol novolak epoxy resin | 43 | 43 | | | | |
| D2: Cresol novolak epoxy resin | | | 50 | 50 | 33 | 33 |

TABLE 3-continued

|  | Comp. Ex. 1 | Comp. Ex. 2 | Comp. Ex. 3 | Comp. Ex. 4 | Comp. Ex. 5 | Comp. Ex. 6 |
|---|---|---|---|---|---|---|
| (Epoxy curing agent) | | | | | | |
| Cresol novolak phenolic resin | | | 10 | 10 | 10 | 10 |
| (E) Inorganic filler | | | | | | |
| Ground silica | 10 | 10 | 10 | 10 | 10 | 10 |
| Aluminum hydroxide | 80 | 80 | 80 | 80 | 80 | 80 |
| Results of determination (evaluation) | | | | | | |
| (1) Adhesion-to-copper foil property (copper foil peeling strength: kN/m) | 0.90 | 0.90 | 0.70 | 0.45 | — | — |
| (2) Glass transition temperature (Tg: ° C.) | 140 | 150 | 130 | 120 | — | — |
| (3) Solder heat resistance | Blister | Blister | Blister | Blister | — | — |
| (4) Copper cladding heat resistance (T-288: min) | 1 | 1 | 1 | 0 | — | — |
| (5) Hygroscopicity (percent water absorption: %) | 1.1 | 1.1 | 0.8 | 1.1 | — | — |
| (6) Flame retardancy | V-0 | V-1 | V-1 | Combustion | — | — |
| (7) Relative dielectric constant (1 GHz) | 4.7 | 4.7 | 5.1 | 5.1 | — | — |
| (8) Dielectric loss tangent (1 GHz) | 0.011 | 0.011 | 0.014 | 0.020 | — | — |

Regarding the carboxyl-group-containing acidic compound (C) shown in Tables 1 to 3, C1: p-hydroxybenzoic acid exhibits an acid dissociation constant (pKa) of 4.08 (reported in the literature) in an infinitely diluted aqueous solution at 25° C., and C2: benzoic acid has an acid dissociation constant (pKa) of 4.00 (reported in the literature) in an infinitely diluted aqueous solution at 25° C.

The employed epoxy resin (D) and epoxy curing agent are as follows:

D1: phenol novolak epoxy resin (trade name: Epiclon N-770, product of Dainippon Ink and Chemicals, Inc.);

D2: cresol novolak epoxy resin (trade name: Epiclon N-673, product of Dainippon Ink and Chemicals, Inc.); and epoxy curing agent: cresol novolak phenolic resin (trade name: KA-1165, product of Dainippon Ink and Chemicals, Inc.).

In Comparative Example 5 or 6, a varnish containing uniformly dissolved thermosetting resin could not be prepared, whereby a prepeg was not produced.

As is clear from Tables 1 to 3, the laminated sheet of each of the Examples—which is formed of a prepreg produced from a thermosetting resin composition containing a curing agent (component (A)) produced through the production method of the present invention—is well-balanced in all of copper foil peeling strength, heat resistance, moisture resistance, flame retardancy, copper cladding heat resistance (T-288), and dielectric properties (relative dielectric constant and dielectric loss tangent).

In contrast, in the case where a thermosetting resin composition contains a curing agent which has an acidic substituent and an unsaturated maleimido group, but which is produced without use of an organic solvent (Comparative Example 1, 2, 4, or 6), in the case where a thermosetting resin composition contains no component (C) (Comparative Example 3), or in the case where the glass transition temperature (Tg) of a thermosetting resin composition does not satisfy the requirement of the present invention (Comparative Example 5), a prepreg cannot be produced. Even through a prepreg is produced, the resultant laminated sheet is not well-balanced in all of copper foil peeling strength, heat resistance, moisture resistance, flame retardancy, copper cladding heat resistance (T-288), and dielectric properties; i.e., the laminated sheet is inferior in any of these properties.

A prepreg produced by impregnating or coating a base with the thermosetting resin composition of the present invention, or a laminated sheet produced through laminate molding of the prepreg is well-balanced in all of adhesion-to-copper foil property, heat resistance, moisture resistance, flame retardancy, copper cladding heat resistance (T-288), and dielectric properties. Therefore, the prepreg or the laminated sheet is very useful for forming a printed wiring board for electronic devices.

INDUSTRIAL APPLICABILITY

A curing agent produced through the method of the present invention has good solubility in an organic solvent and can provide a thermosetting resin composition exhibiting excellent adhesion-to-metal foil property, heat resistance, moisture resistance, flame retardancy, copper cladding heat resistance, and dielectric properties and dielectric loss tangent.

Therefore, according to the present invention, employment of the thermosetting resin composition realizes provision of, for example, a prepreg or laminated sheet exhibiting excellent performance. The prepreg or the laminated sheet is useful for forming, for example, a printed wiring board for electronic devices.

The invention claimed is:

1. A thermosetting resin composition characterized by comprising a curing agent (A) having an acidic substituent and an unsaturated maleimido group, and a compound (B) which is cured with the curing agent, wherein a cured product of the composition has a glass transition temperature of 200° C. or higher, wherein the curing agent (A) is produced through a method characterized by comprising reacting, in an organic solvent, a maleimide compound (a) having at least two N-substituted maleimido groups in a molecule thereof with an amine compound (b) having an acidic substituent represented by the following formula I:

[F1]

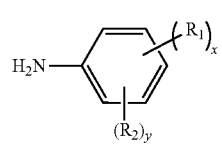

(I)

(wherein $R_1$, which is an acidic substituent, represents a hydroxyl group, a carboxyl group, or a sulfonic acid group; $R_2$ represents a hydrogen atom, a C1-C5 aliphatic hydrocarbon group, or a halogen atom; x is an integer from 1 to 5; y is an integer from 0 to 4; and the sum of x and y is 5), wherein the compound (B) which is cured with the curing agent is an amine compound having at least two primary amino groups in a molecule thereof which is a 6-substituted guanamine compound represented by the following formula (V):

[F5]

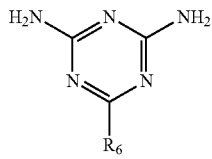

(wherein $R_6$ represents a phenyl group, a methyl group, an allyl group, a butyl group, a methoxy group, or a benzyloxy group), and wherein the composition further contains a carboxyl-group-containing acidic compound (C) having an acid dissociation constant (pKa) of 4.05 or more in an infinitely diluted aqueous solution at 25° C.

2. A thermosetting resin composition as described in claim 1, wherein the curing agent (A) having an acidic substituent and an unsaturated maleimido group is represented by the following formula (II):

[F2]

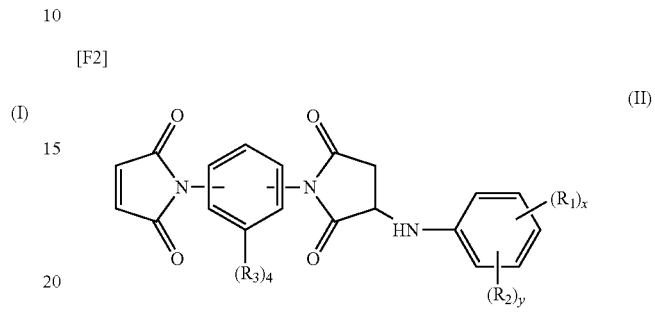

(II)

(wherein $R_1$, $R_2$, x, and y have the same meanings as defined above in formula (I), and $R_3$ represents a hydrogen atom, a C1-C5 aliphatic hydrocarbon group, or a halogen atom); or (III):

[F3]

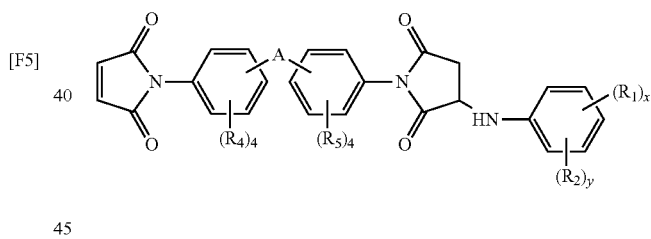

(III)

(wherein $R_1$, $R_2$, x, and y have the same meanings as defined above in formula (I); each of $R_4$ and $R_5$ represents a hydrogen atom, a C1-C5 aliphatic hydrocarbon group, or a halogen atom; A represents an alkylene group, an alkylidene group, an ether group, a sulfonyl group, or a group represented by the following formula (IV)):

[F4]

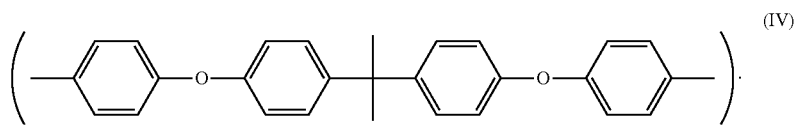

(IV)

3. A thermosetting resin composition as described in claim 1, which further contains an epoxy resin (D) having at least two epoxy groups in a molecule thereof.

4. A thermosetting resin composition as described in claim 1, which further contains an inorganic filler (E).

5. A prepreg produced by impregnating or coating a base with a thermosetting resin composition as recited in claim 1 and B-staging the composition.

6. A laminated sheet produced through laminate molding of a prepreg as recited in claim 5.

* * * * *